US00PP24048P2

(12) United States Plant Patent
de Ruiter

(10) Patent No.: US PP24,048 P2
(45) Date of Patent: Nov. 26, 2013

(54) ***PAEONIA* PLANT NAMED 'HR 01'**

(50) Latin Name: *Paeonia lactiflora*
Varietal Denomination: HR 01

(75) Inventor: Hendrik Marinus de Ruiter, Aalsmeer (NL)

(73) Assignee: De Wilgenhoek Beheer B.V., Aalsmeer (NL)

( * ) Notice: Subject to any disclaimer, the term of this patent is extended or adjusted under 35 U.S.C. 154(b) by 50 days.

(21) Appl. No.: 13/374,972

(22) Filed: Jan. 25, 2012

(51) Int. Cl.
*A01H 5/00* (2006.01)

(52) U.S. Cl.
USPC ..... Plt./316

(58) Field of Classification Search
USPC ..... Plt./316
See application file for complete search history.

*Primary Examiner* — Kent L Bell
(74) *Attorney, Agent, or Firm* — Penny J. Aguirre

(57) ABSTRACT

A new cultivar of *Paeonia* plant named 'HR 01', characterized by its large fully double flowers that are pure white in color and highly fragrant.

2 Drawing Sheets

Botanical classification: *Paeonia lactiflora.*
Variety denomination: 'HR 01'.

BACKGROUND OF THE INVENTION

The present invention relates to a new and distinct cultivar of *Paeonia lactiflora* that will be referred to hereafter by its cultivar name, 'HR 01'. 'HR 01' is an herbaceous perennial suitable for landscape plantings.

The new variety of *Paeonia,* 'HR 01', arose from a controlled cross made by the Inventor in Roelofarendsveen, The Netherlands in May 1980. The cross was made between 'Duchess De Nemour' (not patented) as the female parent and 'Sarah Bernhardt' (not patented) as the male parent. 'HR 01' was selected as a single unique plant in May 1986.

The new cultivar has been asexually propagated by division by the Inventor in Roelofarendsveen, The Netherlands in 1987. Asexual propagation determined that the characteristics of this cultivar are stable and are reproduced true to type in successive generations.

SUMMARY OF THE INVENTION

The following traits have been repeatedly observed and represent the characteristics of the new *Paeonia* as observed for a period of three years in Yamhill, Oreg. and further evaluated at several other test sites in the U.S. These attributes in combination distinguish 'HR 01' as a unique cultivar of *Paeonia.*

1. 'HR 01' exhibits large fully double flowers that are pure white in color.
2. 'HR 01' exhibits flowers that are highly fragrant.

The new cultivar of *Paeonia* can be readily distinguished from its parents and other cultivars. The female parent, 'Duchess De Nemour', is similar to 'HR 01' in having fragrant double white flowers, but differs from 'HR 01' in having petioloids that are light yellow and turn to light green, and in having a more sprawling plant habit. The male parent, 'Sarah Bernhardt', is similar to 'HR 01' in having highly fragrant flowers, however 'Sarah Bernhardt' differs from 'HR 01' in having pink flowers. 'HR 01' can also be compared to the cultivars 'Festiva Maxima' and 'Kelway's Glorious' (both not patented). Both cultivars are similar to 'HR 01' in having large, fragrant white flowers, however 'Festiva Maxima' differs from 'HR 01' in having red flecks on the petaloids and 'Kelway's Glorious' differs from 'HR 01' in having red flecks on the petaloids and opening from rosy pink flower buds.

BRIEF DESCRIPTION OF THE DRAWING

The accompanying colored photographs illustrate the overall appearance and distinct characteristics of a two year-old plant of 'HR 01' as field grown in Roelofarendsveen, The Netherlands.

Figure 1:
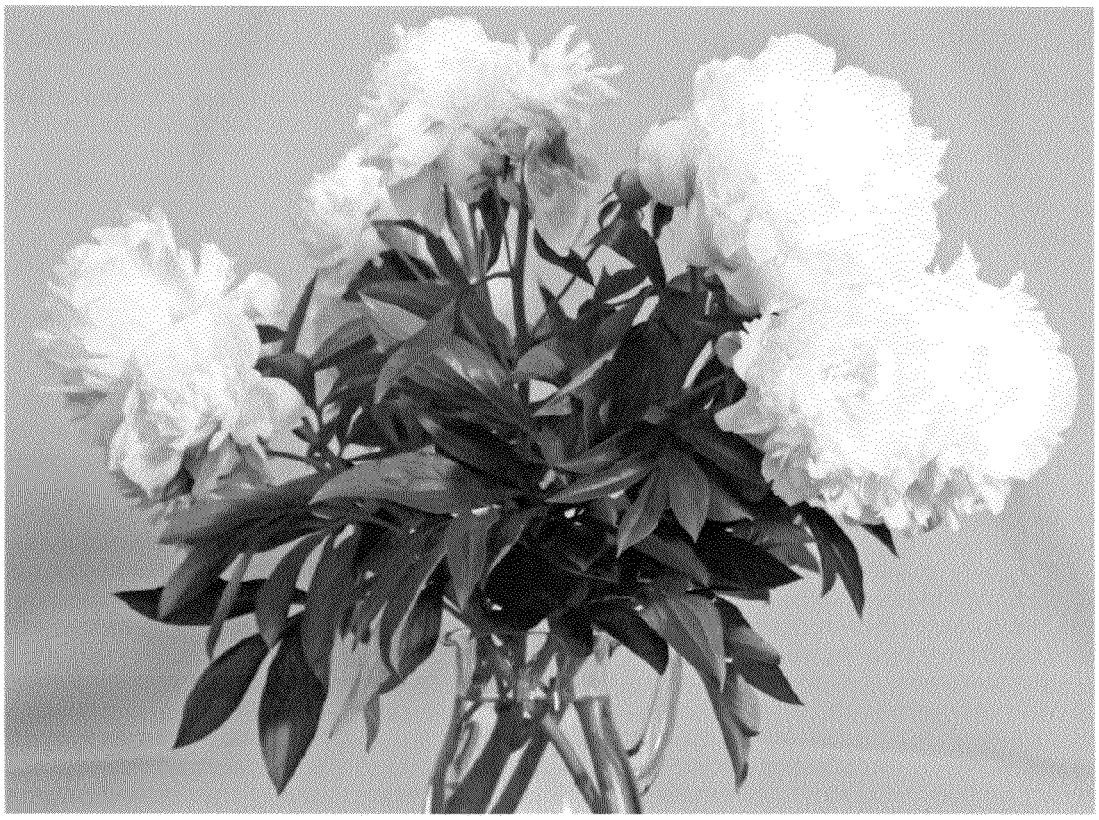
FIG. 1 provides a view of cut stems in a vase.
Figure 2:
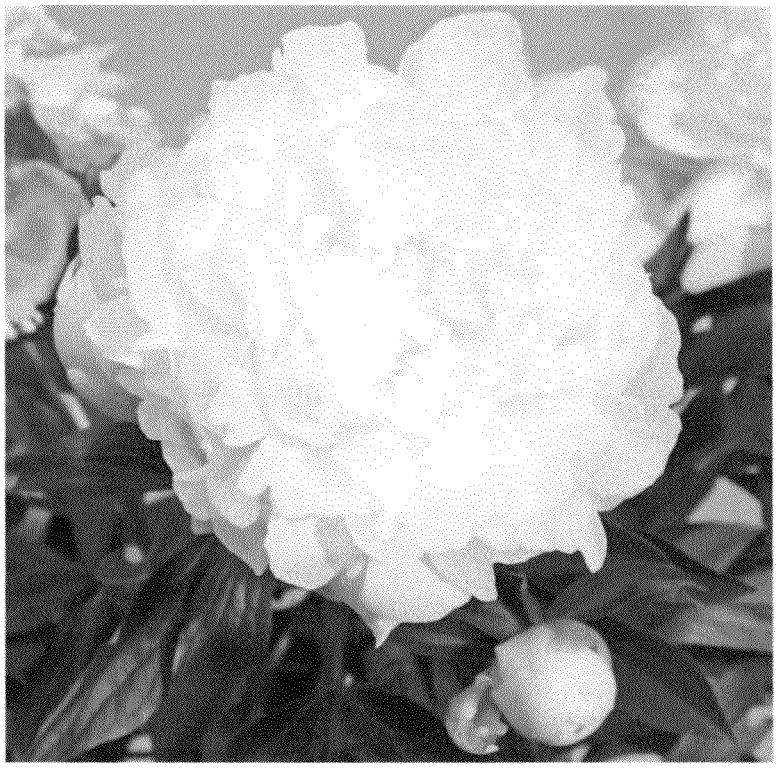
FIG. 2 provides a view of a close-up view of a fully open flower.
Figure 3:
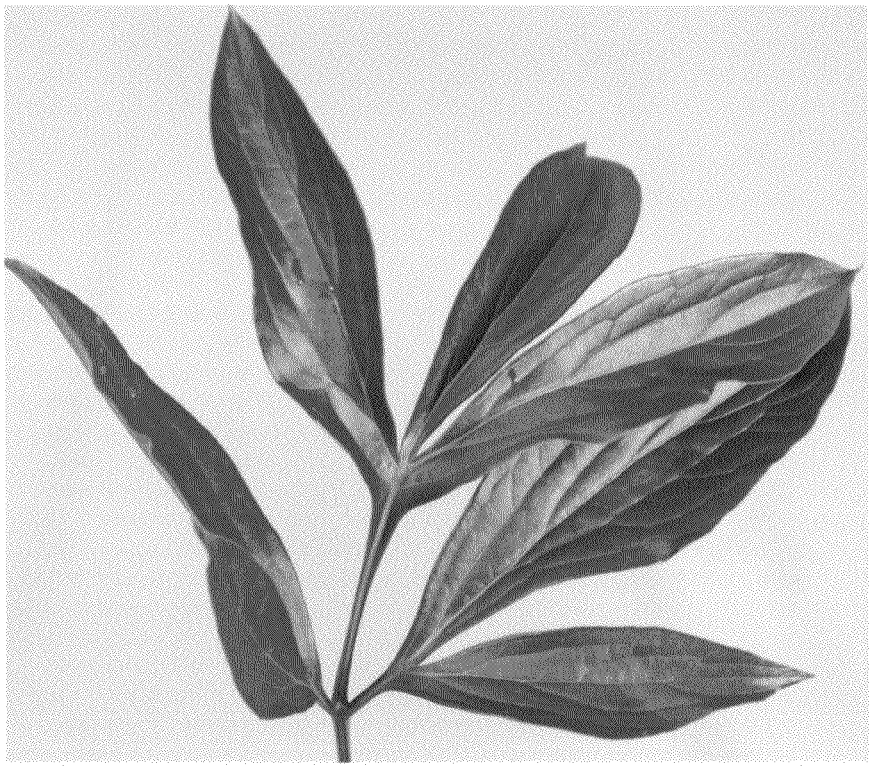
FIG. 3 provides a close-up view of the foliage.

The colors in the photographs are as close as possible with digital photography techniques available, the color values cited in the detailed botanical description accurately describe the colors of the new *Paeonia.*

DETAILED BOTANICAL DESCRIPTION

The following is a detailed description of the new cultivar as observed on two year-old plants of the new cultivar as field grown in Roelofarendsveen, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit.*—May into June in The Netherlands.
*Plant habit.*—Broad upright.
*Height and spread.*—Reaches about 71.5 cm in height and 72.5 cm in spread.
*Cold hardiness.*—At least in U.S.D.A. Zone 4.
*Diseases and pests.*—Not more susceptible to pests and diseases than other herbaceous *Paeonia* varieties.
*Propagation.*—Division.
*Growth.*—Moderately vigorous.

Branch description:

*Stem color.*—144B.

*Stem surface.*—Glabrous, moderately glossy.

*Stem size.*—Average of 8 flowering stems, average of 7 mm in diameter and up to 53.5 cm in length.

*Stem aspect.*—Rounded, slightly angled.

*Stem strength.*—Very strong.

Foliage description:

*Leaves.*—Compound, broad ovate in shape, arrangement is alternate, average of 10 leaves per lateral branch, average of 16.1 cm in length and 19.2 cm in width, internode length is an average of 5 cm.

*Leaflets.*—Typically 3, narrow elliptic to narrow obovate in shape, attenuate base, apiculate apex, entire margins, upper and lower surface is smooth, glabrous and moderately glossy, average of 13.7 cm in length and 8.8 cm in width, color: young leaves upper surface; N137D flushing into 147A, mature leaves upper surface; N137C, young and mature leaves lower surface; 147B, vein color upper surface; 144C tinged at base between 187A to 187B, vein color lower surface; 144B.

*Petioles.*—Average of 7.3 cm in length and 3 mm in diameter, color of upper surface between 183A to 183B, color of lower surface 144B.

Inflorescence description:

*Inflorescence type.*—Upright, simple cyme.

*Flower number.*—Average of 3 per lateral stem.

*Flower fragrance.*—Very strong, acidic-sweet and very pleasant.

*Flower longevity on the plant.*—About 2 weeks.

*Flower longevity as a cut flower.*—10 to 12 days.

*Flower type.*—Fully double.

*Flower size.*—Average of 18 cm in height and 18.4 cm in width.

*Peduncles.*—Strong, average of 10.2 cm in length and 3 mm in diameter, color is 144B, average angle 0° to 20°.

*Calyx.*—Average of 15.9 cm in length and 5.7 cm in width, rotate in shape.

*Flower buds.*—Globular in shape, average of 1.9 cm in length and 2.1 cm in diameter, between 144B to 145B in color.

*Sepals.*—Rotate, average of 5, broadly ovate to obcordate shape, margin is entire, color; young upper surface; between 144B and 145B, mature upper surface 144B, young and mature lower surface; 145A, average of 2.3 cm in length and 2.4 cm in width, base is broad cuneate, apex is rounded to retuse, surface is glabrous on upper and lower surface.

*Petals.*—Average of 10, obovate in shape, surface is velvety and smooth on upper and lower surface, emarginated apex, average of 8.6 cm in length and 6.6 cm in width, color: opening flowers upper and lower surface; between NN155C and NN155D, base; NN155A, fully open flowers upper and lower surface; NN155C.

*Petaloid.*—Average of 200, rotate, narrow to oblanceolate in shape, entire to laciniate margin, average of 6.5 cm in length and 2.5 cm in width, color of young and mature upper and lower surface; between NN155C to NN155D flushing into base and turning into NN155A at base, surface is velvety and smooth on upper and lower surface.

Reproductive organs:

*Stamens.*—About 60, appear deformed, filaments are about 1.6 cm in length and between NN155C and NN155D blending into the base and becoming between 4B and 4C.

*Pistils.*—None present.

It is claimed:

1. A new and distinct cultivar of *Paeonia* plant named 'HR 01' as herein illustrated and described.

* * * * *